United States Patent [19]
Henning et al.

[11] Patent Number: 6,032,059
[45] Date of Patent: Feb. 29, 2000

[54] DEVICE FOR THE DETECTION OF ANALYTE AND ADMINISTRATION OF A THERAPEUTIC SUBSTANCE

[75] Inventors: Timothy P. Henning, Vernon Hills; Eric B. Shain, Glencoe, both of Ill.; Gamal Khalil, Chandler, Ariz.; Tuan A. Elstrom, Lake Bluff, Ill.

[73] Assignee: Abbott Laboratories, Abbott Park, Ill.

[21] Appl. No.: 08/898,209

[22] Filed: Jul. 22, 1997

Related U.S. Application Data

[62] Division of application No. 08/574,880, Dec. 19, 1995, abandoned.

[51] Int. Cl.[7] .................................................. A61B 5/05
[52] U.S. Cl. ........................ 600/345; 600/573; 600/584
[58] Field of Search ................................ 604/19, 27–28, 604/30–45, 49, 51, 131, 133, 134, 140, 141, 890.1, 891.1; 128/DIG. 12, 898; 600/345

[56] References Cited

U.S. PATENT DOCUMENTS

| | | |
|---|---|---|
| 4,020,830 | 5/1977 | Johnson et al. . |
| 4,882,492 | 11/1989 | Schlager . |
| 4,953,552 | 9/1990 | DeMarzo . |
| 5,043,286 | 8/1991 | Khalil et al. . |
| 5,209,231 | 5/1993 | Cote et al. . |
| 5,243,982 | 9/1993 | Mostl et al. . |
| 5,368,571 | 11/1994 | Horres, Jr. .................. 128/DIG. 12 |
| 5,383,452 | 1/1995 | Buchert . |
| 5,568,806 | 10/1996 | Cheney II et al. . |
| 5,582,170 | 12/1996 | Soller . |
| 5,799,660 | 9/1998 | Bertone .................................. 128/898 |

FOREIGN PATENT DOCUMENTS

| | | |
|---|---|---|
| 0309214 | 3/1989 | European Pat. Off. . |
| 0317847 | 5/1989 | European Pat. Off. . |
| 0401179 | 12/1990 | European Pat. Off. . |
| 4123441 | 1/1992 | Germany . |
| 9413203 | 6/1994 | WIPO . |
| 9522057 | 8/1995 | WIPO . |
| 9116416 | 10/1996 | WIPO . |

OTHER PUBLICATIONS

B.H. Ginsberg, "An Overview of Minimally Invasive Technologies", *Clinical Chemistry*, vol. 38, No. 9, (1992), pp. 1596–1600.

U.S. Pat. Application Number 08/563,728, filed Dec. 18, 1995 to T.P. Henning for "Interference Free Biosensor".

*Primary Examiner*—Cary O'Connor
*Assistant Examiner*—Ryan Carter
*Attorney, Agent, or Firm*—David L. Weinstein; Gregory W. Steele

[57] ABSTRACT

The present invention relates to a device for the sampling of blood or other body fluids which includes means for the direct measurement of the analyte of interest within the fluid. Also disclosed is a 'closed-loop' device and method wherein the analyte is measured and the required amount of drug is determined and injected, without removal of the device from the patient's body.

5 Claims, 3 Drawing Sheets

DEVICE FOR THE DETECTION OF ANALYTE AND ADMINISTRATION OF A THERAPEUTIC SUBSTANCE

This application is a division of U.S. patent application Ser. No. 08/574,880, filed Dec. 19, 1995, abandoned.

FIELD OF THE INVENTION

This disclosure is in the field of blood glucose monitoring. Specifically, the invention relates to a device for the sampling of blood and the determination of glucose therein. Optionally, the device also incorporates a means for administering insulin to the patient.

BACKGROUND OF THE INVENTION

The ability to accurately measure analytes in the blood, particularly glucose, is important in the management of diseases such as diabetes. Blood glucose levels must be maintained within a narrow range (about 3.5–6.5 mM). Glucose levels lower than this range (hypoglycemia) may lead to mental confusion, coma, or death. High glucose levels (hyperglycemia) cause excessive thirst and frequent urination. Sustained hyperglycemia has been linked to several of the complications of diabetes, such as kidney damage, neural damage, and blindness.

Blood glucose is maintained in many diabetics with routine injections of insulin. Unlike the normal functioning of the body's glucose control systems, injections of insulin incorporate no feedback mechanisms. Controlling glucose levels therefore requires continuous or frequent measurements of blood glucose concentration in order to determine the proper amount and frequency of insulin injections.

Conventional glucose measurement techniques require a part of the body (normally a fingertip) be lanced, milking the finger to produce a drop of blood at the impalement site, and depositing the drop of blood on a measurement device (such as an analysis strip). This lancing of the finger, at typical measurement frequencies of two to four times a day, is both painful and messy for the patient. The pain and inconvenience has additional and more serious implications of noncompliance, in that many patients will not maintain the recommended regimen of blood glucose measurement and thereby run the risk of improper glucose levels and consequent harmful effects.

In short, the inherent limitations of conventional blood glucose measurement techniques mean that patients either suffer this pain and inconvenience or neglect glucose monitoring and suffer the adverse physiological effects of improper glucose control. Thus there is a clear need for a glucose measurement technique that minimizes or eliminates pain and inconvenience to the patient.

One of the methods of reducing the pain and inconvenience of glucose measurement to a patient is to replace the typical lancet with the use of a hollow needle. Needle use has been reported as less painful than lancet use (B. H. Ginsberg, An overview of minimally invasive technologies, *Clinical Chemistry* 38:1596–1600, 1992). The pain of sampling is further reduced by withdrawing blood through the needle rather than milking the finger, which involves further pain and soreness. Finally, the containment of the blood in the needle yields a much cleaner and convenient test than conventional techniques which require dripping or smearing blood on a test strip.

Currently known glucose measurement devices that use needles are of two types. The first, such as that described in U.S. Pat. No. 4,953,552, use a needle that remains implanted in the body for an extended period of time—several days, in this case. The second type, such as that described in International Patent Publication 94/13203, uses a needle with an electrochemical sensor integrated into its tip. This second type does not withdraw blood or other body fluids and must still be left in the patient's body tissue for 5–100 seconds in order to measure the output signal from the sensor.

The present disclosure provides an advantage over the existing needle glucose sensors described above in that it comprises a hollow needle with which blood is withdrawn from the patient for monitoring. The use of the needle minimizes the pain and inconvenience to the patient. The withdrawal of blood with the needle allows the needle to be rapidly withdrawn from the patient's body.

The present disclosure also describes a glucose injector. Since blood glucose measurement is normally performed prior to insulin injection, this invention optionally allows both the measurement and the injection to be made with a single needle penetration, further reducing the pain to the patient.

SUMMARY OF THE INVENTION

Figure 1:
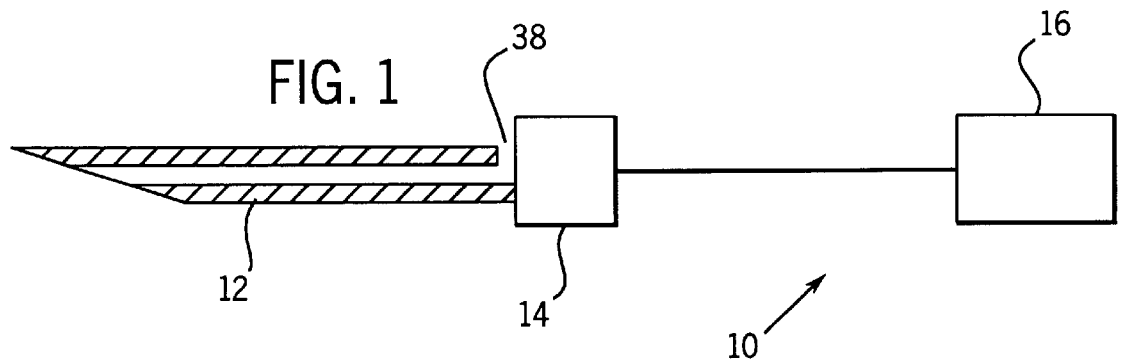
FIG. 1 shows one embodiment of the invention.

The present disclosure provides a fluid sampling device for sampling fluid from a patient, the device comprising a sampling needle, a sensor included in the sampling needle which detects an analyte of interest in the fluid, and an analysis means which receives and processes a signal from the sensor.

In its preferred form, the above embodiment employs a sensor which is an electrochemical sensor or, more preferably, an optical sensor for the detection of glucose. When an electrochemical sensor is employed, an enzyme may be immobilized in a resin. When an optical sensor is employed, an enzyme may be immobilized in a membrane and the membrane located on an optical conduit, e.g., a fiber optic conduit.

Additional embodiments include an analysis means which includes a display function, and a 'closed-loop' system whereby the above described device includes a control device for receiving a signal from the analysis means and for transmitting a signal to an injection actuator, and an injector for delivering the required amount of a drug of interest in response to the injection actuator.

Further, additional, features of the 'closed-loop' embodiments include those where the control device includes a user input or an analytical method for determining the required amount of the drug to be injected.

Also disclosed is a device for delivering a drug directly to the body of a patient, comprising a control device for transmitting a signal to an injection actuator, and an injector for delivering the required amount of the drug in response to the injection actuator, wherein the injector includes a needle. Additional and optional features include those where the control device includes a user input or analytical method for determining the required amount of the drug to be injected.

Also disclosed is a method of sampling fluid from a patient, comprising providing a sampling device of the invention, introducing the sampling needle into the patient, and allowing the fluid to come into contact with the sensor whereby the presence or amount of an analyte of interest in the fluid is detected and the results transmitted to the analysis means for processing.

Also provided is a method of sampling fluid and delivering a drug to a patient, comprising providing a 'closed-loop' device of the invention, introducing the sampling needle into the patient, and allowing the fluid to come into contact with the sensor whereby the presence or amount of an analyte of interest in the fluid is detected and the results transmitted to the analysis means for processing, transmitting the results of the processing to a control device for transmitting a signal to an injection actuator, and delivering the required amount of the drug in response to the injection actuator, via the sampling needle.

Further, disclosed is a method of delivering a drug directly to the body of a patient, comprising providing a drug delivery device which comprises a control device for transmitting a signal to an injection actuator, and an injector for delivering the required amount of the drug in response to the injection actuator, the injector including a needle, introducing the injector into the patient, and delivering the required drug dosage in response to the injection actuator.

DETAILED DESCRIPTION OF THE INVENTION

The fluid sampling device of the invention generally comprises a fluid sampling apparatus 10, including a hollow sampling needle 12, a sensor 14, and an analysis device 16, as illustrated in FIG. 1.

In operation (not shown), the sampling needle is used to penetrate the skin at any convenient location, e.g., a finger or a less innervated location such as the thigh or upperarm. Blood or other body fluid flows into the needle by capillary action and/or other hydrodynamic forces. A vent hole 38 may be used to facilitate the flow of fluid into the needle and may be incorporated in the needle 12, as shown in FIG. 1, or elsewhere within the device, see, e.g., FIG. 3. The fluid is allowed to flow into the needle until it comes into fluidic contact with sensor 14. In a preferred embodiment, the needle 12 is mounted on the analysis device 16, and the user impales his finger or another convenient part of his body with the needle 12 by pressing this finger onto the needle 12.

The hollow sampling needle 12 is of any dimension suitable for the intended use. Preferably a 26 gauge needle, having an internal dimension of about 250 µm, is employed. Such needles are readily available from a number of commercial sources.

Figure 2:
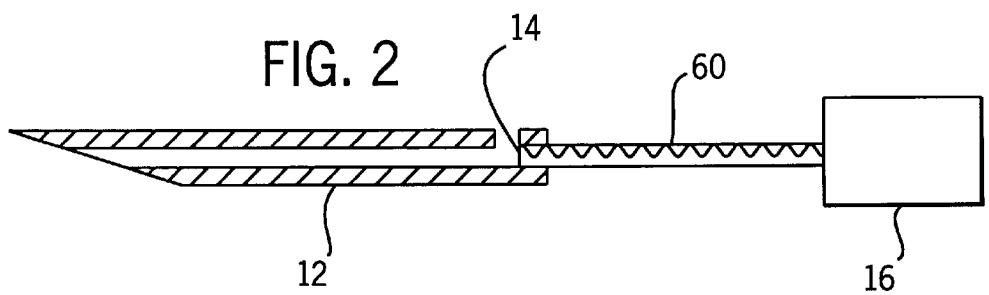
FIG. 2 shows an alternative embodiment of the invention.

The sensor 14 may be an electrochemical sensor, optical sensor, or any other type of analytical sensor designed to determine the concentration of a desired analyte within the blood or other body fluid. FIG. 2, for example, illustrates the preferred optical sensor 14 mounted on the end of a fiber optic conduit 60 which conveys optical information to the analysis means 16. In an alternate embodiment, FIG. 3, the analysis is performed by an analytical instrument (not shown) that acquires data by the transmission of visible, infra-red, or other light through a transparent housing 40 filled by the body fluid extracted by the needle 12. In FIG. 4, an electrochemical sensor 14 is mounted in the needle 12. Appropriate electrical insulation 42 and electrical connections 44 enable the electrochemical detector 14 to convey information to the analysis device 16.

The analysis means 16 is generally an electronic, preferably microprocessor controlled, device capable of receiving and processing an electronic, optical, or other signal from the sensor 14 and displaying the concentration of the analyte of interest for the user. The analysis means may be programmed with factory-set calibration curves or may be calibrated by the user with the use of calibrator and control solutions having known concentrations of the analyte of interest contained therein. Optionally, and preferably, the analysis means 16 also includes a display means such that the concentration of the analyte of interest in the patient's bodily fluid is displayed in a manner which is useful to the user, e.g., mg of glucose per deciliter of blood. The display means can be visual, via a liquid crystal display, for example, or aural and can include a printed record. Furthermore, the analysis device can include means for storing the results, such that the user or the user's physician can later retrieve the results for analysis, compliance, etc.

Figure 5:
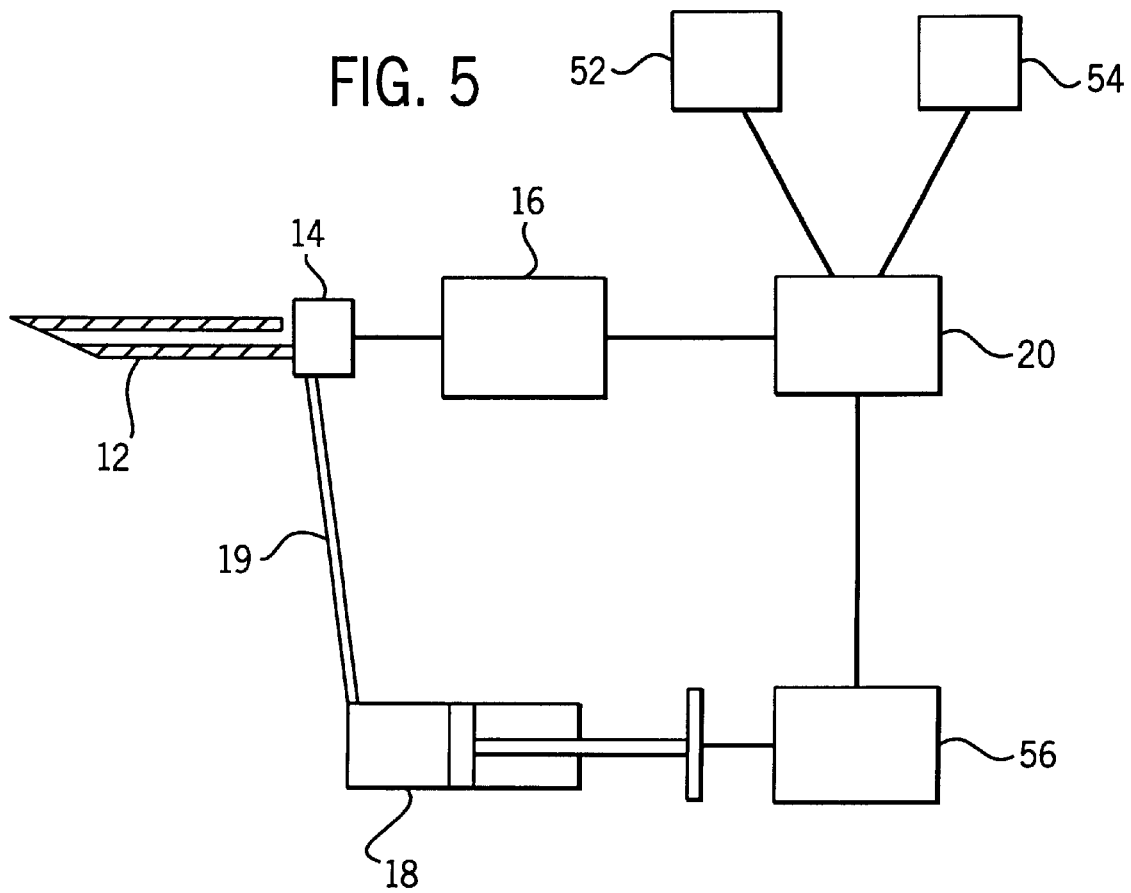
FIG. 5 shows an alternative embodiment of the invention including an injection system.

In an exemplary embodiment, FIG. 5, the sampling device described above is coupled to an injection device 18 in order to deliver insulin to the patient. Thus in a single penetration of the skin the patient can receive both information regarding glucose levels within the body as well as deliver, if necessary, the required amount of insulin. In this embodiment, the analysis means 16 also sends an electronic signal representative of the concentration of the analyte of interest to a control device 20. Optionally, the control device 20 may also be configured to receive an electronic signal from a user input device 52 and/or from a stored control algorithm 54. The function of the control device is to generate an output signal for an injection actuator 56. The injection actuator 56 controls the operation of the injection device 18 which is fluidically connected to the sampling needle 12 via a fluid conduit 19. For example, the sensor 14 may be a sensor designed to detect the concentration of glucose in the blood or other body fluid. The analysis means 16 sends a signal to the control device 20 indicative of this glucose concentration. The user may read the glucose concentration from the analysis means 16 and control the injection of insulin via the user input 52. Alternatively, a stored control algorithm 54 may automatically calculate the required amount of insulin based on the output of the analysis means 16, e.g., the concentration of glucose in the blood. In either case, the control device 20 sends a signal representing the required injection of insulin to the injection actuator 56. The injection actuator may be, for example, a linear actuator that controls the operation of a plunger in the injection device 18. In this case, the injection actuator 56 causes the plunger in the injection device 18 to move by the amount corresponding to the required amount of the insulin injection. As the plunger in the injection device moves, the insulin is injected via the sampling needle 12, effecting the sampling, analysis, and control of blood glucose with a single skin penetration.

EXAMPLE 1

Detection of Glucose

An embodiment of the invention may be used to measure the concentration of glucose in a patient's blood. Using an embodiment of the device similar to that illustrated in FIG. 2, the patient inserts the pointed end of the needle 12 into a convenient part of his body. Blood flows into the needle 12 due to capillary action and other hydrodynamic forces, coming in contact with a glucose sensor 14. The needle 12 may then be withdrawn. The sensor 14 may be a sensor that optically measures the interaction of the glucose with a sensing medium. For example, the sensor may consist of glucose oxidase and catalase immobilized in the pores of a membrane. In the presence of a solution containing glucose, the glucose is oxidized and a corresponding amount of oxygen is depleted. The depletion of oxygen may be measured through the use of a luminescent substance as is described in U.S. Pat. No. 5,043,286. Thus, the depletion of oxygen corresponds to the concentration of glucose in the patient's blood. In a preferred embodiment, the sensor 14 is miniaturized to the extent that it can be located on the end of a fiber optic or other optical conduit 60.

In a preferred embodiment, an optical glucose sensor may be constructed as follows.

Step 1—Amination of Silica. Add 1 gram of fumed silica (Sigma Chemical, St. Louis) to a centrifuge tube and add 8.0 grams of sterile water. Add 2.0 grams of 3-Amino propyl triethoxy silane ((AP)TES) (Sigma, St. Louis Mo.) to the tube and vortex thoroughly until all the silica is in solution. Add 1 ml of 6N HCl (Anachemia, Rouses Point N.Y.) and vortex. Heat the reaction mixture in the 70 C water bath for 1 hour, and vortex the solution. Centrifuge and decant the supernatant three times, each time adding 40 ml of sterile water and vortexing the solution following the decanting.

Step 2—Immobilization of Catalase to Aminated Silica. 4.7 mg of catalase (bovine liver, Sigma, St. Louis Mo.) is added into 0.75 ml of PESK 7.5 (a solution of 100 mM NaCl, 50 mM sodium phosphate, 1 mM EDTA, 0.05% Kathon CG antimicrobial (Rohm and Haas, Philadelphia Pa.) solution at a pH of 7.5). 12.5 mg of 1,2,4,5 Benzenetetracarboxylic acid dianhydride (PMA) (Aldrich, Milwaukee Wis.) is added to 1 ml of PESK 7.5. Suspend the PMA by vortexing. Add 50 μL of the PMA solution to the enzyme solution, vortex, and rotate for 1 hour at room temperature. Add 0.75 ml of aminated silica solution (25 mg/ml of silica). Centrifuge and decant supernatant three times, each time adding 1 ml of 50 mM 2[N-Morpholino]ethane sulfonic acid (MES) (Sigma, St. Louis Mo.), pH 5.5 and vortexing. Add 1.5 mg of 1-Ethyl-3-(3-dimethylaminopropyl) carbodiimide HCl (EDC) (Pierce, Rockford Ill.) and rotate for 1 hour. Centrifuge and decant supernatant twice, adding 1 ml of sterile water each time and vortexing the solution after the first addition of sterile water.

Step 3—Immobilization of Glucose Oxidase to Aminated Silica. Weigh 25 mg of glucose oxidase (aspergillus niger, Boehringer Mannheim, Indianapolis Ind.) into 2.5 ml of PESK 7.5. Add 2.5 mg of 1,2,4,5 Benzenetetracarboxylic acid dianhydride (PMA) (Aldrich, Milwaukee Wis.) to the glucose oxidase solution. The solution is vortexed and rotated for 1 hour at room temperature. Add 5 ml of aminated silica solution (25 mg/ml silica). Centrifuge and decant supernatant three times, each time adding 4 ml of 50 mM MES , pH 5.5, and vortex solution following the decanting. Add 5 mg of EDC and rotate for 1 hour. Centrifuge and decant supernatant three times, adding 4 ml of PESK 7.5 after each decanting and vortexing the solution after all but the final addition of sterile water.

Step 4—Resin Formulation. A resin matrix, termed F133 resin, for retaining the immobilized enzyme to a sensor surface is made by combining the following weights of each component:

| | |
|---|---:|
| Joncryl 537 (Johnson Wax, Racine WI) | 65.04 mg |
| NH$_4$OH, 10% in water | 8.91 mg |
| 2-Ethoxy-ethanol (Aldrich, Milwaukee WI) | 20.94 mg |
| Dibutyl Phthalate (Fluka, Rokonkonia NY) | 7.13 mg |
| Surfynol 104H (Air Products, Allentown PA) | 2.50 mg |
| Surfynol 695 (Air Products) | 5.0 mg |
| Acrysol 275 (Rohm and Haas, Philadelphia PA) | 30.6 mg |

80 mg of the liquid resin is combined with 15 mg immobilized catalase, 134 mg immobilized glucose oxidase, and 347 mg water containing 0.085 M trehalose (Sigma, St. Louis, Mo.). A vigorous mixing of the three components is done by violent shaking using an amalgamator (WIG-L-BUG, Crescent Dental Co., Lyons Ill.) for 3 minutes. This resin and other suitable alternatives are disclosed in International Patent Publication WO 95/22057. The method described therein incorporates the particles into a resin matrix (also referred to as "paint") and has the benefits of being water based to preserve enzyme activity. It also yields a liquid, facilitating dispensing and ease of manufacture. One microliter of the paint is dispensed onto a polycarbonate membrane (Poretics, Livermore Calif.) with 0.6 micron diameter pores. The drop is spread across the surface of the membrane to wet the pores. The surface is then wiped with a tissue, leaving only the paint in the pores. The paint is then allowed to dry in the pores forming a water insoluble matrix to retain the glucose oxidase and catalase.

Figure 6:
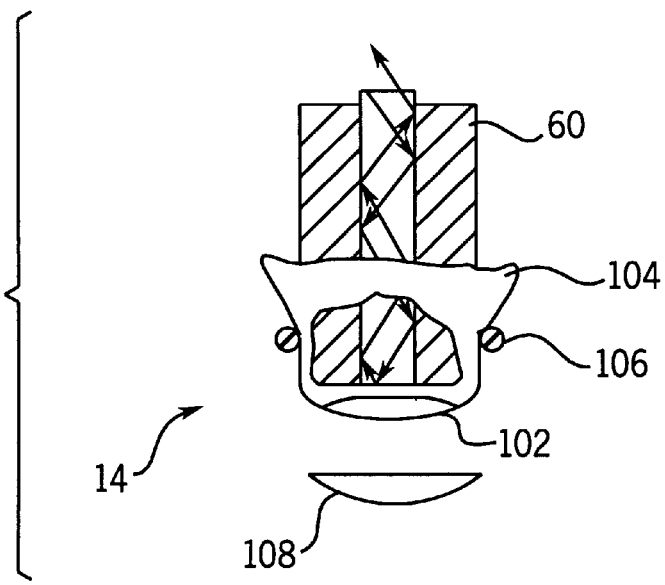
FIG. 6 shows an oxygen sensor useful in embodiments of the invention.
Figure 7:
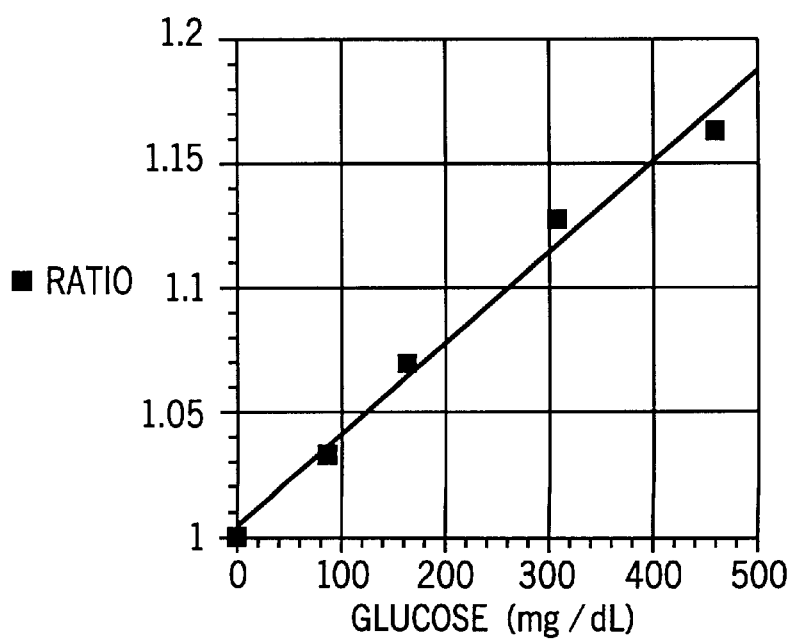
FIG. 7 shows the results obtained using an oxygen sensor as described in FIG. 6.

Step 5—Construction of the oxygen sensor. An oxygen sensitive dye solution is prepared by dissolving 100 mg of platinum tetrapentafluorophenyl porphine (Pt(TFPP)) (Porphyrin Products, Logan Utah) in 25 ml of a silicone polymer stock solution. The latter is made by dissolving 10 grams of a dimethylsiloxane-bisphenol A-polycarbonate blockcopolymer (GE, Waterford, N.Y.) in 100 ml tetrahydrofuran. One microliter of the dye solution is dispensed on a polycarbonate membrane 104 (Poretics, Livermore Calif.) with 0.4 micron diameter pores. The solution is allowed to dry. As illustrated in FIG. 6, the membrane 104 containing the oxygen sensitive dye 102 is wrapped around the end of a 250 micron fiber optic cable 60. The membrane 104 is secured to the cable with a small O-ring 106. A second membrane 108 containing the enzyme in the paint matrix is placed on top of the membrane 104 containing the oxygen sensitive dye. Membrane 108 is also secured with a small O-ring (not shown).

The oxygen sensor operates as follows: Pt(TFPP) dye adsorbs light at <570 nm and has a phosphorescent emission centered at 650 nm. Because oxygen quenches the emission, the lifetime of the emission depends on the amount of oxygen present. The lifetime of the emission is therefore a function of the oxygen concentration. The lifetime of the emission is quantified by comparing the amount of light emitted at short times (about 0–20 μsec) with that at long times (about 0–270 μsec). The ratio of the two signals (long time/short time) is the measured output and this ratio increases with decreasing levels of oxygen. The oxygen concentration, in turn, is affected by the concentration of glucose due to the presence of the glucose oxidase and catalase.

A probe is made as described above with an oxygen sensitive dye membrane next to the fiber optic bundle and an enzyme containing membrane on top of the dye membrane. The probe is dipped into solutions containing various levels of glucose in phosphate buffered saline of pH 7.5 at 37 C. The response of the sensor to various levels of glucose is recorded for two minutes and the results illustrated in FIG.

7. A good correlation coefficient of 0.993 is found for the graph of the ratio versus the glucose concentration with a slope of 0.000353 and Y-intercept of 1.004. These results indicate that a sensor on a 250 micron fiber optic bundle is useful for the measurement of glucose concentrations, and is useful in embodiments of this invention.

EXAMPLE 2

Optical Detection of Glucose

Figure 3:
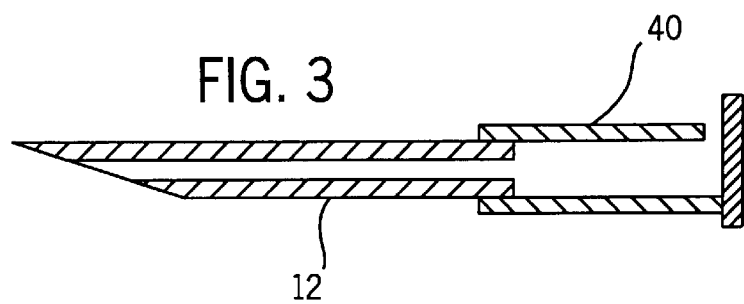
FIG. 3 shows an alternative embodiment of the invention.
Figure 4:
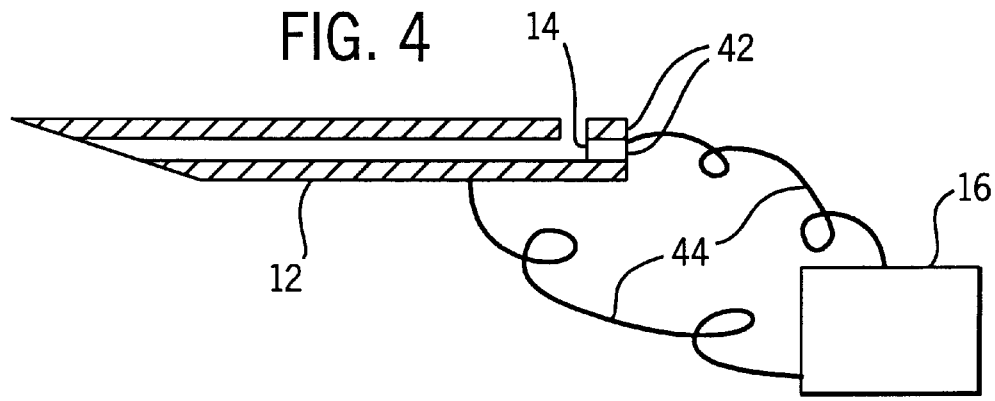
FIG. 4 shows an alternative embodiment of the invention.

In an additional embodiment of the invention, similar to that show in FIG. 3, the needle 12 is inserted into a convenient part of the patient's body. Blood or other body fluid flows into the needle 12 due to capillary action and/or other hydrodynamic forces, filling the chamber surrounded by the optically transparent housing 40. The needle 12 may then be withdrawn from the patient's body, and the needle and housing assembly may be placed in or adjacent to an optical analytical instrument (not shown). Such instruments measure the concentration of glucose or another analyte of interest by means of directing a beam of visible, infra-red, or other light through the transparent housing 40 filled with the blood or other body fluid. Descriptions of analytical techniques that may be employed with this embodiment are found in U.S. Pat. Nos. 5,209,231 (measurement of glucose concentration via polarization measurements), 5,383,452 (measurement of glucose concentration via the detection of intrinsic luminescence polarization), and 4,882,492 (measurement of glucose concentration via subtractive correlation spectroscopy of reflected or transmitted near infrared light). Additional analytical means will be apparent to those skilled in the art, or will become apparent upon reading the present disclosure.

EXAMPLE 3

Electrochemical Detection of Glucose

A further embodiment of the invention uses a device similar to that illustrated in FIG. 4. In this embodiment, the sensor 14 is an electrochemical sensor mounted inside the needle that detects the concentration of glucose in the blood. An example of such a sensor is that described in a copending U.S. Patent Application filed on even date herewith (Attorney Docket number 5843.US.01).

EXAMPLE 4

Glucose Sampling and Insulin Infusion

A further optional embodiment of the invention is used to measure the concentration of glucose in the blood and automatically inject the required amount of insulin or other therapeutic substance. Using an embodiment of the device similar to that illustrated in FIGS. 2 or 4, the patient inserts the needle 12 into a convenient part of his body. Blood flows due to capillary action and/or other hydrodynamic forces into the needle 12 until it reaches the sensor 14. In this embodiment, the needle 12 remains inserted in the body. The sensor 14 is an electrochemical sensor or optical sensor mounted inside the needle that detects the concentration of glucose in the blood and sends a signal representing this concentration via the analysis means 16 to the control device 20, as illustrated in FIG. 5. The control device 20, operating as directed by the patient via the user control 52 or a stored algorithm 54 or both, sends a signal to the injection actuator 56 indicating the required amount of insulin. The actuator 56 causes the injection device 18 to inject the required amount of insulin via the sampling needle 12. During the injection, a valve (not shown) may close the vent hole 38 to ensure that the insulin is injected into the patient.

All of the references cited in this application are incorporated by reference. The present invention has been described with reference to preferred and/or alternate embodiments. One of skill in the art will readily appreciate that changes, alterations or modifications can be made to these embodiments without departing from the true scope and spirit of the invention.

We claim:

1. A device for delivering a drug directly to the body of a patient, comprising:
    (a) a needle for taking us blood or other body fluid from a patient by means of capillary action or other hydrodynamic forces or by means of both capillary action and other hydrodynamic forces;
    (b) a sensor included in the needle, which sensor detects an analyte of interest or concentration thereof in the blood or other body fluid;
    (c) an analysis means for receiving and processing a signal from the sensor and sending a signal representative of the analyte of interest or the concentration thereof to (d) a control device for transmitting a signal to an injection actuator; and
    (e) an injector for delivering the required amount of the drug in response to the injection actuator via the needle.

2. The device of claim 1 wherein the control device includes a user input for determining the required amount of the drug to be injected.

3. The device of claim 1 wherein the control device includes an analytical method for determining the required amount of the drug to be injected.

4. The device of claim 3 wherein the analytical method is an algorithm.

5. A method of delivering a drug directly to the body of a patient, comprising:
    (a) providing (1) a needle, which needle is capable of taking up blood or other body fluid from a patient by means of capillary action or other hydrodynamic forces or by means of both capillary action and other hydrodynamic forces; (2) a sensor included in the needle, which sensor detects an analyte of interest or concentration thereof in the blood or other body fluid; (3) an analysis means for receiving and processing a signal from the sensor and sending a signal representative of the analyte of interest or the concentration thereof to a control device for transmitting a signal to an injection actuator;
    (b) providing a drug delivery device which comprises the control device for transmitting a signal to the injection actuator, and an injector for delivering the required amount of the drug in response to the injection actuator via the needle;
    (c) introducing the needle into the patient; and
    (d) delivering the required drug dosage in response to the injection actuator.

* * * * *